United States Patent [19]

Brugger

[11] Patent Number: 5,322,516
[45] Date of Patent: Jun. 21, 1994

[54] SAFETY NEEDLE SYSTEM AND METHOD FOR USING THE SAME

[75] Inventor: James M. Brugger, Boulder, Colo.

[73] Assignee: Cobe Laboratories, Inc., Lakewood, Colo.

[21] Appl. No.: 65,118

[22] Filed: May 20, 1993

[51] Int. Cl.$^5$ .............................................. A61M 5/32
[52] U.S. Cl. .................................. 604/192; 604/264; 128/765
[58] Field of Search ............... 604/167, 117, 272, 239, 604/86, 88, 169, 83, 264, 48, 192, 93; 128/763-767

[56] References Cited

U.S. PATENT DOCUMENTS

| | | |
|---|---|---|
| 1,180,665 | 4/1916 | McElroy . |
| 2,512,568 | 6/1950 | Saffir . |
| 3,823,840 | 7/1974 | Zackheim . |
| 3,853,127 | 12/1974 | Spademan . |
| 3,977,403 | 8/1976 | Patel . |
| 3,994,293 | 11/1976 | Ferro . |
| 4,197,848 | 4/1980 | Garrett et al. . |
| 4,475,548 | 10/1984 | Muto . |
| 4,634,424 | 1/1987 | O'Boyle . |
| 4,673,393 | 6/1987 | Suzuki et al. . |
| 4,790,830 | 12/1988 | Hamacher . |
| 4,809,679 | 3/1989 | Shimonaka et al. . |
| 4,819,684 | 4/1989 | Zaugg et al. . |
| 4,838,877 | 6/1989 | Massau . |
| 4,915,687 | 4/1990 | Sivert . |
| 4,954,149 | 9/1990 | Fullermann . |
| 5,049,128 | 9/1991 | Duquette . |
| 5,080,654 | 1/1992 | Picha et al. . |
| 5,092,840 | 3/1992 | Healy ............................. 604/83 |
| 5,135,489 | 8/1992 | Jepson et al. ..................... 604/48 |
| 5,135,489 | 8/1992 | Jepson et al. . |

FOREIGN PATENT DOCUMENTS

WO90/01349 2/1990 PCT Int'l Appl. .

Primary Examiner—C. Fred Rosenbaum
Assistant Examiner—Vanitha Alexander
Attorney, Agent, or Firm—Jay K. Malkin

[57] ABSTRACT

A medical system for transferring fluids (e.g. blood) to or from patients which includes a needle having a proximal end, a distal end attached to a syringe (or other comparable fluid transfer device), a medial section, and an internal passageway. The medial section is elliptical in cross-section with dual arcuate side walls. The proximal end is blunt and rounded. Also included is an access site having a conduit with a resilient tubular port extending outwardly therefrom. The port includes a bore therethrough. The port and the bore are both elliptical in cross-section. A resilient compression member having an elliptical opening therein is positioned on the port to exert pressure thereon and close the bore. In use, the needle is urged into the bore, temporarily deforming the compression member. After removing or delivering fluids using the syringe (or other device), the needle is withdrawn from the bore which is self-sealing by the compressive action of the compression member.

18 Claims, 2 Drawing Sheets

SAFETY NEEDLE SYSTEM AND METHOD FOR USING THE SAME

BACKGROUND OF THE INVENTION

The present invention generally relates to medical components used for fluid transfer, and more particularly to a specialized safety needle apparatus, an access site for use therewith, and a method wherein the foregoing components may be used to deliver or withdraw fluids (e.g. blood) from a patient in a safe and effective manner.

In recent years, the medical community and the general public have become increasingly concerned regarding the proliferation of various fluid-transmissible diseases. For example, one disease of substantial concern is Acquired Immune Deficiency Syndrome (otherwise known as "AIDS"). According to current research, the AIDS virus is transmitted through various forms of contact with bodily fluids, including but not limited to blood. Thus, should a medical professional accidently experience tissue penetration by a needle used to extract blood from a patient, a significant risk of AIDS virus transmission exists. The transfer or extraction of bodily fluids (especially blood) from patients by medical personnel must therefore be undertaken with a considerable degree of care and caution.

Traditional techniques for withdrawing blood and other bodily fluids have involved the use of conventional syringe units each having a sharply pointed needle attached thereto. No matter how carefully this type of system is used, accidental needle penetration and the subsequent infection of medical personnel is always a possibility. Furthermore, even if direct needle penetration does not occur, conventional fluid extraction systems may allow blood or other bodily fluids to leak therefrom during use. As a result, medical personnel may experience skin contact with the blood or other fluids, thereby presenting a risk of infection (especially if protective gloves and other safety devices are not being used).

A number of attempts have been made to design fluid transfer components (e.g. syringes, needles, access sites, and the like) which minimize the risk of disease transfer and infection of medical personnel. For example, U.S. Pat. No. 5,135,489 to Jepson et al. discloses a blood sampling system which involves the use of a septum-type pre-slit access site adapted to receive a blunt cannula operatively connected to a syringe. U.S. Pat. No. 5,092,840 to Healy involves the use of a valved medication container which enables medicine to be withdrawn and transferred to the inlet valve of an intravenous tube without the use of a needle, thereby minimizing the risk of disease transmission. U.S. Pat. No. 4,915,687 to Sivert discloses a needleless injection port system for intravenous fluid transfer which is particularly designed to reduce the risk of AIDS virus transmission. Published PCT Application No. WO 90/01349 discloses a hollow needle having a closed blunt end and an orifice spaced along the longitudinal axis of the needle from the closed end thereof. Other injection devices, devices used to transfer bodily fluids (e.g. blood), and systems for administering medical compositions to patients are disclosed in U.S. Pat. Nos. 5,080,654; 5,049,128; 4,954,149; 4,838,877; 4,819,684; 4,809,679; 4,790,830; 4,673,393; 4,634,424; 4,475,548; 4,197,848; 3,994,293; 3,977,403; 3,853,127; 3,823,840; 2,512,568; and 1,180,665.

Notwithstanding the inventions described in the foregoing references, a considerable need remains for a safety needle apparatus which effectively eliminates the possibility of accidental needle penetration and infection of medical personnel. Likewise, a need remains for a safety needle apparatus and access site which allow bodily fluids (e.g. blood) to be withdrawn from a patient in a safe and rapid manner without fluid leakage. The present invention satisfies these needs in a highly effective manner, as described in greater detail below.

SUMMARY OF THE INVENTION

It is an object of the present invention to provide a medical system for the safe and effective transfer of bodily fluids (e.g. blood).

It is another object of the invention to provide a medical system which substantially eliminates the possibility of disease transmission from a patient to medical personnel during bodily fluid (e.g. blood) extraction or introduction.

It is another object of the invention to provide a medical system which involves the use of a specialized, blunt safety needle designed to avoid accidental needle penetration and infection of medical personnel.

It is a further object of the invention to provide a blunt safety needle characterized by a substantially flat appearance with enables fluids to be transferred with a high degree of safety while minimizing the possibility of fluid leakage.

It is a still further object of the invention to provide a unique, highly specialized access site which is adapted to receive the safety needle of the present invention in an efficient manner in order to minimize the possibility of fluid leakage between the needle and the access site.

It is an even further object of the invention to provide a highly specialized access site and safety needle for use therewith which are readily manufactured on a mass-production basis using a minimal number of production steps.

It is an even further object of the invention to provide a highly specialized access site and safety needle for use therewith which accomplishes all of the foregoing goals while providing a medical system which is easily used in a effective manner by medical personnel.

In accordance with the foregoing objects, the present invention involves a medical system for transferring bodily fluids (e.g. blood) in a safe and effective manner. In particular, the medical system set forth herein enables bodily fluids to be handled (e.g. withdrawn or introduced) in a manner wherein accidental needle penetration of medical personnel, as well as undesired fluid leakage are substantially avoided.

The medical system of the present invention basically involves two main components. First, a needle apparatus is provided which consists of a body portion having a proximal end, a distal end, and a medial section therebetween. The needle apparatus is designed for attachment to a conventional medical fluid transfer device used to administer or withdraw fluids (e.g. blood) to or from a patient. The term "medical fluid transfer device" as used herein shall broadly encompass a wide variety of conventional components used to withdraw or deliver fluid materials to patients. An exemplary and preferred medical fluid transfer device for use with the needle apparatus of the present invention is a conventional syringe having a reservoir chamber with a first end, a second end, and a slidable plunger positioned within the chamber. The plunger is also of conventional construction, and includes a resilient, movable seal member positioned within the chamber with an elongate handle member connected to the seal member. At least a portion of the handle member extends outwardly from the second end of the reservoir chamber so that the handle and seal members may be moved as desired. Other exemplary medical fluid transfer devices shall include but not be limited to commercially available fluid transfer containers having a vacuum therein, as well as conventional fluid infusion lines, catheters, and the like.

Extending continuously through the body portion of the needle apparatus from the proximal end to the distal end thereof is an elongate passageway designed to enable fluid transfer through the needle apparatus. The medial portion of the needle apparatus is elliptical in cross-section as specifically defined herein, thereby creating a flat external appearance. This cross-sectional configuration also assists in minimizing the possibility of leakage during fluid withdrawal from a patient, as will be described in greater detail below.

The needle apparatus of the present invention is preferably manufactured of an inert, resilient, and flexible material (e.g. plastic). The proximal end thereof comprises a blunt, rounded terminal portion which substantially eliminates accidental penetration of the needle apparatus into a user. Likewise, in a preferred embodiment, the proximal end of the needle apparatus (and the terminal portion thereof) are both elliptical in cross-section.

The distal end of the needle apparatus preferably includes a cavity therein sized to receive at least a portion of a conventional fluid transfer device (e.g. a syringe). If a syringe is involved, the cavity in the distal end of the needle apparatus is designed to receive the first end of the reservoir chamber of the syringe so that it may be secured to the needle apparatus in a convenient and effective manner.

In accordance with the elliptical configuration of the medial section of the needle apparatus, the medial section further includes a first side wall and a second side wall which are fixedly secured to each other in order to form an integral structure. The first side wall and the second side wall each include an arcuate exterior surface. In a preferred embodiment and in order to produce the desired elliptical configuration (e.g. flat appearance) of the needle apparatus as described herein, the arcuate exterior surface of the first side wall and the arcuate exterior surface of the second side wall both have a substantially equal radius of curvature. Furthermore, in a preferred embodiment, the medial section includes a first elongate linear edge portion and a second elongate linear edge portion, both extending continuously from the proximal end of the body portion to the distal end thereof. As illustrated and described herein, the first side wall and the second side wall are positioned between the first and second elongate linear edge portions.

Next, the medical system of the present invention includes an access site assembly uniquely configured for use in connection with the above-described needle apparatus. In a preferred embodiment, all of the components of the access site assembly are manufactured from an inert, resilient, and flexible material (e.g. plastic). The access site assembly specifically consists of a tubular main conduit having a first end, a second end, and an intermediate section between the first and second ends. Also included is a passageway extending continuously through the intermediate section of the main conduit from the first end to the second end thereof. In a preferred embodiment, the first end of the main conduit is designed for the receipt of one end of a first fluid transfer tube which is operatively connected at its opposite end to the circulatory (e.g. vascular) system of a patient. Likewise, the second end of the main conduit is designed for the receipt of one end of a second fluid transfer tube which (in a preferred embodiment) is operatively connected at its opposite end to a supply of liquid medicine or other desired therapeutic fluid.

The access site assembly of the present invention further includes an elongate flexible tubular access port extending outwardly from the intermediate section of the main conduit (preferably at about a 90° angle thereto). The access port has an elongate bore therethrough in fluid communication with the above-described passageway. In a preferred embodiment, both the access port and the bore therein are elliptical in cross-section, with the bore being sized to receive the proximal end of the needle apparatus and a portion of the medial section thereof in a secure manner. Specifically, the cross-sectional dimensions of the bore are only as large as are necessary to receive the needle apparatus therein, and no larger. As a result, fluid leakage between the access site assembly and the needle apparatus will be prevented.

In addition, the access site assembly includes a resilient, semi-rigid, deformable compression member having an opening therethrough. The term "deformable" as used herein shall involve a structure which may be stretched to a limited degree and will return to its original configuration without permanent deformation. The compression member is positioned on the tubular access port (which is flexible as indicated above) so that the access port passes through the opening in the compression member. The compression member is preferably circular or elliptical in cross-section, with the opening therethrough being elliptical in cross-section. Prior to placement of the compression member in position on the access site assembly, the access port is designed so that it remains in an open, expanded configuration wherein the access port and bore therethrough are both elliptical in cross-section as noted above. After placement of the compression member on the access port, the access port is compressed by the compression member so that the bore (and the access port) are maintained in a closed configuration. As a result, access through the bore is entirely restricted. Specifically, the opening through the compression member has a size sufficiently small to enable the semi-rigid compression member to engage and compress the flexible access port. As a result, the bore through the access port is effectively closed (e.g. sealed) when the access site assembly is not being used.

In a preferred embodiment, the tubular access port further includes an inner end, an outer end, and a medial portion between the inner and outer ends. As described in detail below, the inner end is fixedly secured to (e.g. integrally formed with) the intermediate section of the main conduit. The outer end of the access port includes a flange (preferably elliptical in cross-section) extending outwardly therefrom. The compression member is positioned on the medial portion of the access port between the inner end and the outer end, with the flange preventing premature, unintended detachment of the compression member from the access port.

In operation (with the compression member being positioned on the tubular access port), fluid passing through or residing within the intermediate section of the main conduit may be withdrawn in a highly safe and effective manner. To accomplish this, the needle apparatus is attached to the selected medical fluid transfer device (e.g. a syringe). If a syringe is used, the handle member of the plunger in the syringe is then urged inwardly, thereby forcing the seal member within the reservoir chamber toward the first end of the chamber. Next, the proximal end of the needle apparatus is positioned above and in axial alignment with the bore in the access port (which is in a closed configuration as noted above due to the exertion of compressive forces by the compression member on the side walls of the access port). The proximal end (e.g. the terminal portion) of the needle apparatus is then urged into the bore of the access port, thereby forcing the needle apparatus into the bore and causing a temporary deformation of the compression member. The proximal end of the needle apparatus is continuously urged inward until it is immersed within the fluid passing through or residing within the intermediate section of the main conduit. At this point, the proximal end of the needle apparatus is positioned entirely within the access site assembly (e.g. within the intermediate section of the main conduit), with a portion of the medial section of the needle apparatus being positioned within the bore of the access port. The handle member of the plunger within the reservoir chamber of the syringe is then pulled outwardly, thereby causing the seal member to move toward the second end of the reservoir chamber. As a result, a vacuum is created within the reservoir chamber which causes fluid from the access site assembly to be pulled through the needle apparatus and into the chamber. As this occurs, fluid leakage between the access port and the needle apparatus (e.g. the medial section thereof) is prevented by constant compression of the side walls of the access port against the needle apparatus by the deformed compression member. Fluid leakage is further controlled by the mating cross-sectional design (e.g. elliptical configuration) of the bore in the access port and the medial section of the needle apparatus. Specifically, secure engagement of these components is accomplished by virtue of the elliptical configuration thereof which enables precise mating engagement of the needle apparatus and the bore in a highly effective manner compared with the use of non-elliptical components.

The needle apparatus is then pulled outwardly from the bore in the tubular access port. Again, during this operation, fluid leakage is prevented by the compression member which compresses the access port against the needle apparatus, thereby creating a dynamic seal between these components. After the needle apparatus is removed, the bore immediately returns to a closed configuration due to further compressive forces exerted by the compression member against the side walls of the access port. As a result, fluid remaining within the intermediate section of the main conduit is prevented from leaking outwardly through the bore in the access port. Finally, accidental tissue penetration of medical personnel by the needle apparatus is effectively prevented due to the blunt character of the proximal end (e.g. terminal portion) thereof.

These and other objects, features, and advantages of the present invention shall be described below in the following Brief Description of the Drawings and Detailed Description of Preferred Embodiments.

DETAILED DESCRIPTION OF PREFERRED EMBODIMENTS

The present invention involves a unique and highly effective medical system for the transfer of bodily fluids (e.g. blood) from a patient. While the invention shall be described below with primary reference to the withdrawal of fluid samples from a patient, the term "transfer" as used herein shall also broadly include the introduction of various fluids (e.g. liquid medicines) and the like into a patient for therapeutic purposes. Accordingly, the present invention shall not be limited with respect to its intended purposes and the environment in which it may be used.

The present invention provides numerous important benefits. Primarily, the needle apparatus disclosed herein is particularly designed to eliminate the possibility of accidental needle penetration into medical personnel during the treatment of patients. Of particular concern is the avoidance of needle penetration during blood sample extraction. As noted above, many serious blood transmissible diseases exist including but not limited to Acquired Immune Deficiency Syndrome ("AIDS"). The needle apparatus of the present invention is particularly designed to avoid the use of sharp points and edges, thereby eliminating the risk of accidental needle penetration. Furthermore, the access site assembly described herein (which is designed for exclusive use with the foregoing needle apparatus) effectively prevents fluid leakage between the needle apparatus and the access site assembly. As a result, the infection of medical personnel by direct contact with contaminated bodily fluids (e.g. blood) is prevented. Furthermore, the access site assembly of the present invention is self-sealing so that, after the needle apparatus is removed therefrom, blood or other bodily fluids residing within the access site assembly will not leak outwardly therefrom. The present invention therefore represents a considerable advance in the art of medical fluid transfer technology, as described in greater detail below.

Figure 1:
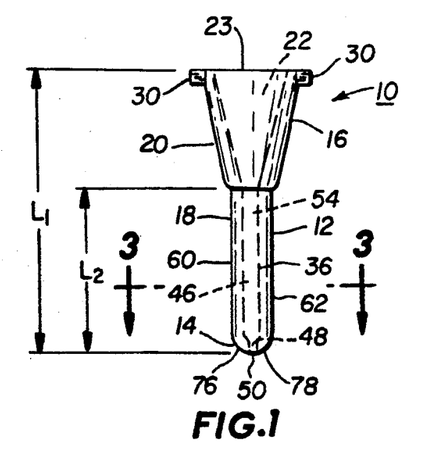
FIG. 1 is an enlarged front view of a safety needle apparatus produced in accordance with the present invention.
Figure 2:
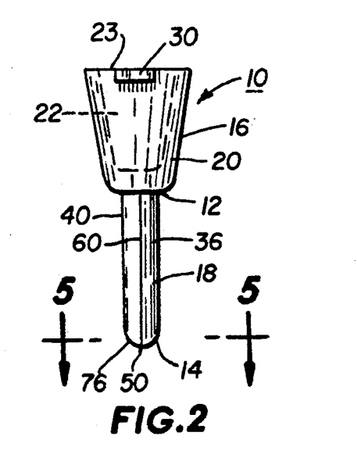
FIG. 2 is a side view of the needle apparatus of FIG. 1.

With reference to FIGS. 1 and 2, a needle apparatus 10 produced in accordance with the present invention is generally illustrated (in enlarged format for the sake of clarity). The needle apparatus 10 basically includes a body portion 12 having a proximal end 14, a distal end 16, and a medial section 18 between the proximal end 14 and the distal end 16. The distal end 16 includes a frustoconical section 20 having a substantially conical interior cavity 22 therein which is open at the top end 23 thereof. The cavity 22 is adapted to receive at least a portion of a conventional medical fluid transfer device 40 (e.g. a syringe, intravenous infusion line, etc.) therein as will be described in greater detail below.

In addition (as shown in FIGS. 1 and 2) the top end 23 of the frustoconical section 20 will include a plurality (preferably two) of tabs 30 integrally formed thereon. The tabs 30 are again designed to facilitate attachment of the needle apparatus 10 to a conventional syringe or other fluid transfer device as discussed below.

Figures 3, 4, 5, 6, 7, 8, 9:
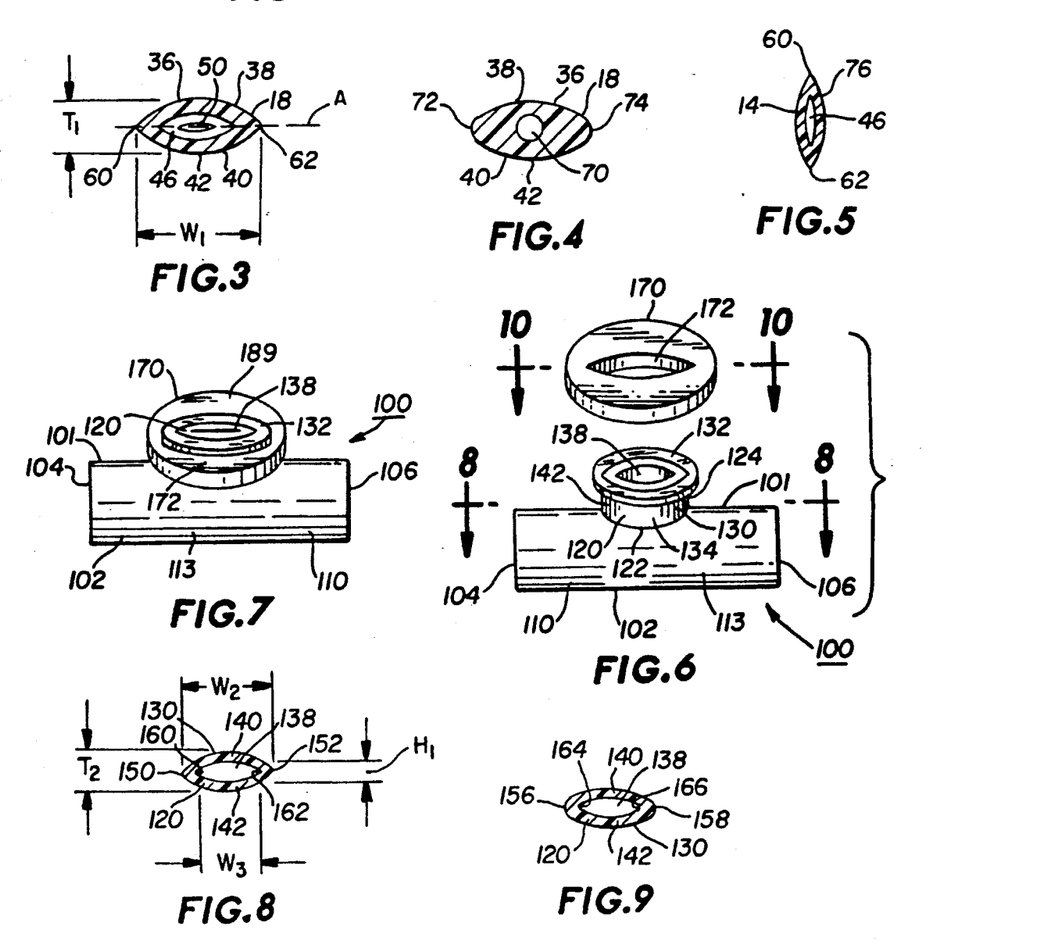
FIG. 3 is a cross-sectional view of the needle apparatus of FIG. 1 taken along line 3—3 of FIG. 1 which is further enlarged for the sake of clarity.
FIG. 4 is a cross-sectional view of the needle apparatus of FIG. 1 taken along line 3—3 of FIG. 1 which has been modified in accordance with an alternative embodiment of the present invention which is further enlarged for the sake of clarity.
FIG. 5 is a cross-section view of the needle apparatus of FIG. 2 taken along line 5—5 of FIG. 2 showing the terminal portion at the proximal end of the needle apparatus which is further enlarged for the sake of clarity.
FIG. 6 is a partially exploded front enlarged perspective view of an access site assembly designed for use in connection with the needle apparatus of FIG. 1 wherein the tubular access port of the access site assembly is shown in an open configuration (e.g. prior to engagement of the access port within its associated resilient compression member).
FIG. 7 is a front enlarged perspective view of the access site assembly of FIG. 6 wherein the tubular access port thereof is shown in a closed configuration (e.g. after placement of the resilient compression member on the access port).
FIG. 8 is a cross-sectional view of the tubular access port in the access site assembly of FIG. 6 taken along line 8—8 thereof.
FIG. 9 is a cross-sectional view of the tubular access port in the access site assembly of FIG. 6 taken along line 8—8 thereof which has been modified in accordance with an alternative embodiment of the present invention.

The medial section 18 of the needle apparatus 10 is preferably uniform in size and cross-sectional configuration along its entire length as illustrated in FIGS. 1-3. In a preferred embodiment, the medial section 18 is uniformly elliptical in cross-section along its entire length as specifically shown in FIGS. 2 and 3 so that the body portion 12 has a substantially flat visual appearance. With continued reference to FIG. 3, the medial section 18 includes a first side wall 36 having an arcuate exterior surface 38 and a second side wall 40 having an arcuate exterior surface 42. So that the medial section 18 is entirely symmetrical in structure and appearance, the exterior surface 38 of the first side wall 36 and the exterior surface 42 of the second side wall 40 each have a substantially equal radius of curvature (e.g. the same degree of curvature). In accordance with this relationship, the medial section 18 is symmetrical along line "A" as illustrated in FIG. 3.

Passing entirely through the medial section 18 of the needle apparatus 10 is an elongate passageway 46 which, in a preferred embodiment, is elliptical in cross-section along its entire length. The passageway 46 further includes a first end 48 which terminates at an outlet 50 in the proximal end 14 of the body portion 12 as shown in FIG. 1. Likewise, the passageway 46 includes a second end 54 which is in fluid communication with the cavity 22 in the distal end 16 of the needle apparatus 10. The passageway 46 is uniformly sized along its entire length except at the first end 48 thereof where it preferably diminishes in width and thickness as illustrated in FIGS. 1 and 5.

With continued reference to FIGS. 1-3, the term "elliptical" as used herein shall encompass a cross-sectional configuration wherein the first and second side walls 36, 40 terminate in a first elongate linear edge portion 60 and a second elongate linear edge portion 62, with the first and second side walls 36, 40 being positioned between the first and second elongate linear edge portions 60, 62 as illustrated in FIG. 3. Furthermore, in a preferred embodiment, the first and second elongate linear edge portions 60, 62 extend continuously along the entire length of the medial section 18.

FIG. 4 involves a cross-sectional view of the medial section 18 of the needle apparatus 10 which has been modified in accordance with an alternative embodiment of the present invention. Specifically, an alternative passageway 70 is shown which (unlike passageway 46) is circular in cross-section along its entire length. Furthermore, the embodiment of FIG. 4 does not include the first and second elongate linear edge portions 60, 62 as illustrated in FIG. 3. Instead, the medial section 18 in the embodiment of FIG. 4 includes a first curved edge portion 72 and a second curved edge portion 74. The first and second curved edge portions 72, 74 extend continuously along the entire length of the medial section 18 in the same manner set forth above relative to the first and second elongate linear edge portions 60, 62. In addition, the term "elliptical" as used herein with respect to the medial section 18 and all other components of the present invention shall likewise encompass the cross-sectional configuration of the medial section 18 presented in FIG. 4 which is entirely curved at all points along the exterior surface thereof as shown.

With continued reference to FIGS. 1-2, the proximal end 14 of the needle apparatus 10 tapers (e.g. narrows) progressively inward to thereby form a terminal portion 76 having outlet 50 therein. The terminal portion 76 at the proximal end 14 of the needle apparatus 10 has a blunt, rounded end 78 as illustrated in FIG. 1. This design (e.g. the use of a terminal portion 76 having a blunt, rounded end 78) effectively prevents accidental penetration of medical personnel with the needle apparatus 10 during use. As noted above, this aspect of the invention is of primary importance, especially with respect to preventing the transmission of viral diseases including but not limited to AIDS.

Furthermore, in a preferred embodiment, the terminal portion 76 is preferably elliptical in cross-section along its entire length, and progressively decreases in size toward outlet 50. A cross-sectional view of the terminal portion 76 of proximal end 14 showing the elliptical character thereof is presented in FIG. 5. Likewise, in a preferred embodiment as illustrated in FIGS. 2 and 5, the first and second elongate linear edge portions 60, 62 continuously extend along the proximal end 14 and terminal portion 76 until the end 78 is reached.

The length "$L_1$" (FIG. 1) of the entire needle apparatus 10 may be selectively varied during production of the apparatus 10, although it is preferred that the length "L₁" be about 0.45-1.00 inches. Likewise, the length "L₂" (FIG. 1) of the medial section 18 and the proximal end 14 (in combination) may be selectively varied during production of the apparatus 10, although it is preferred that the length "L₂" be about 0.35-0.60 inches. Furthermore, the width "W₁" (FIG. 3) of the medial section 18 may also be varied during manufacture of the apparatus 10, although it is preferred that the width "W₁" be about 0.10-0.30 inches. Finally, as shown in FIG. 3, the thickness "T₁" of the medial section 18 may likewise be varied during production, although it is preferred that the thickness "T₁" be about 0.05-0.15 inches. It should be noted that the foregoing dimensions are listed for example purposes only, and the present invention shall not be limited to the specific values set forth above. Furthermore, it is preferred that the needle apparatus 10 be of single piece (e.g. unitary) construction and manufactured from a resilient, flexible, and inert material as indicated above. An exemplary construction material suitable for this purpose would include but not be limited to a plastic such as polyethylene or polypropylene. Also, to achieve a maximum degree of safety, the needle apparatus 10 is designed for a single use, and is discarded thereafter.

Another important component of the medical system of the present invention is a specialized access site assembly generally designated at reference number 100 in FIGS. 6-7. The access site assembly 100 is particularly designed for use with the needle apparatus 10. Specifically, the combined use of access site assembly 100 and needle apparatus 10 enables bodily fluids (e.g. blood) to be withdrawn from a patient in safe manner with substantially no leakage or spillage of the bodily fluids being withdrawn.

Figures 10, 11, 12:
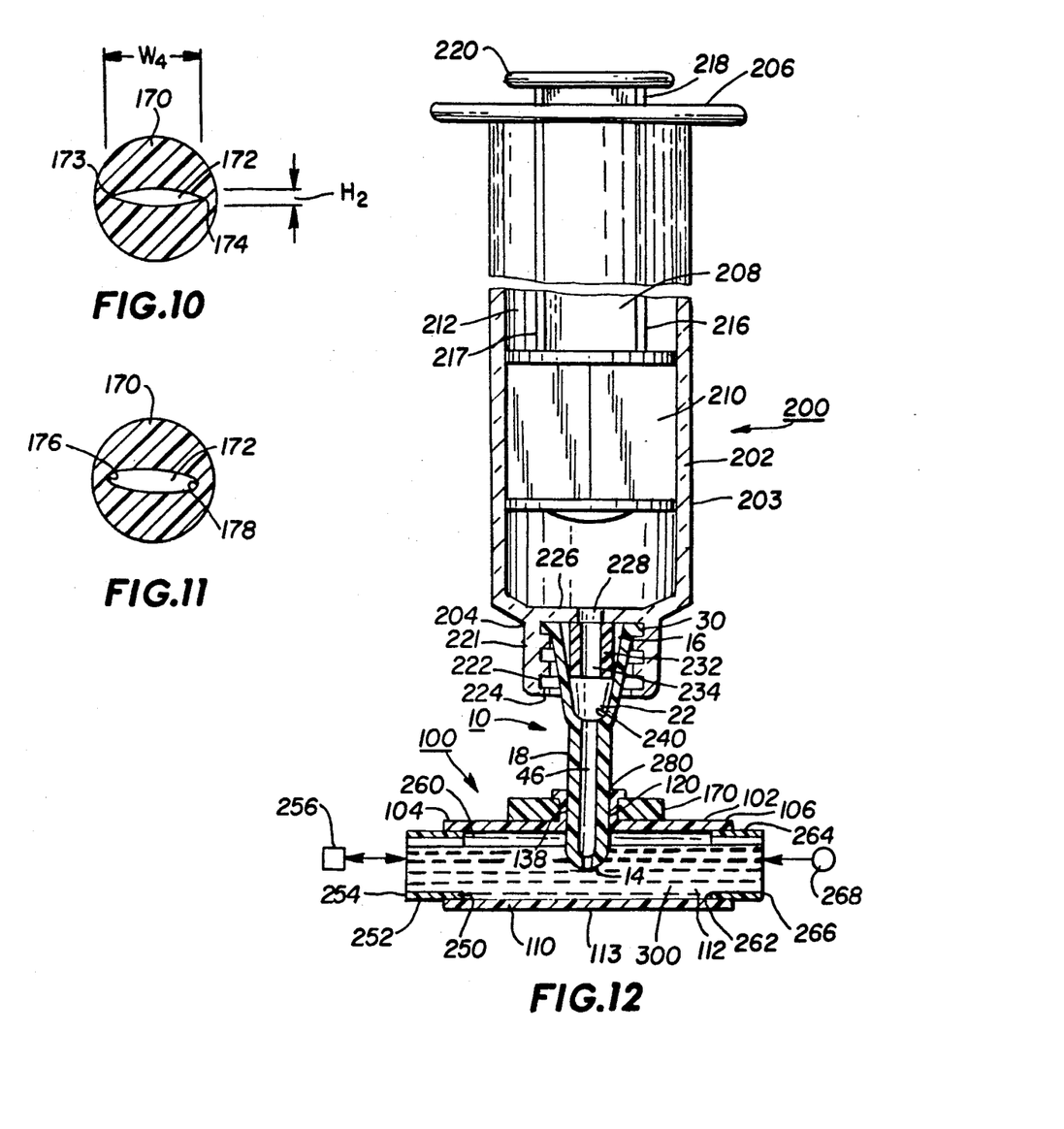
FIG. 10 is an enlarged cross-sectional view of the resilient compression member of FIG. 6 taken along line 10—10 thereof.
FIG. 11 is an enlarged cross-sectional view of the resilient compression member of FIG. 6 taken along line 10—10 thereof which has been modified in accordance with an alternative embodiment of the present invention.
FIG. 12 is an enlarged cross-sectional view of the access site assembly of FIG. 7 having the needle apparatus of claim 1 positioned therein during a fluid withdrawal procedure, with the needle apparatus being attached to a conventional syringe shown partially in cross-section.

With reference to FIGS. 6, 7, and 12, the access site assembly 100 includes a housing 101 having an elongate, tubular main conduit 102 with an open first end 104, an open second end 106, and an intermediate section 110 between the first and second ends 104, 106. In a preferred embodiment, the main conduit 102 is uniformly circular in cross-section along its entire length. In addition, the term "tubular" as used herein shall generally signify an elongate structure having a bore or passageway therethrough surrounded by a continuous wall. In this regard, the main conduit 102 further includes a passageway 112 therein which is surrounded by a continuous, annular side wall 113 (FIG. 12). As illustrated, the passageway 112 extends continuously through the intermediate section 110 from the first end 104 to the second end 106.

Extending outwardly from the intermediate section 110 and fixedly secured thereto (e.g. integrally formed therewith) is an elongate, upwardly-extending tubular access port 120 (FIG. 6). The access port 120 has an inner end 122 immediately adjacent the intermediate section 110 of the main conduit 102 and an outer end 124. Positioned between the inner end 122 and the outer end 124 is a medial portion 130 illustrated in FIG. 6. In addition, fixedly secured to (e.g. integrally formed with) the outer end 124 of the tubular access port 120 is an outwardly extending flange 132, the function of which will be described hereinafter. As shown in FIG. 6, the flange 132 (preferably elliptical in cross-section) extends outwardly beyond the exterior surface 134 of the medial portion 130 of the access port 120. Finally, in accordance with the tubular character of the access port 120, the port 120 further includes a bore 138 extending continuously therethrough (FIGS. 6, 8, and 12). The bore 138 extends entirely through the medial portion 130 from the inner end 122 to the outer end 124, and is in uninterrupted fluid communication with the passageway 112 through the main conduit 102.

In a preferred embodiment, the medial portion 130 of the tubular access port 120 will be uniformly elliptical in cross section from the inner end 122 to the outer end 124 as illustrated in FIGS. 6 and 8. Furthermore, it is preferred that the bore 138 likewise be uniformly elliptical in cross-section (FIG. 8) along its entire length. The width "W₂" and the thickness "T₂" of the access port 120 as shown in FIG. 8 may be selectively varied during production of the access site assembly 100. However, in a preferred embodiment, the width "W₂" will be about 0.20-0.50 inches, and the thickness "T₂" will be about 0.15-0.35 inches. Also, in a preferred embodiment, the tubular access port 120 will actually consist of an arcuate first side wall 140 fixedly secured to an arcuate second side wall 142 (FIG. 8) with the bore 138 therebetween. Furthermore, the first and second side walls 140, 142 preferably terminate in a first elongate linear edge portion 150 and a second elongate linear edge portion 152, with the first and second side walls 140, 142 being positioned between the edge portions 150, 152 as illustrated in FIG. 8. In a preferred embodiment, the elongate linear edge portions 150, 152 extend continuously along the entire length of the access port 120 from the inner end 122 to the outer end 124 thereof.

FIG. 9 illustrates a cross-sectional view of the medial portion 130 of the tubular access port 120 which has been modified in accordance with an alternative embodiment of the present invention. Specifically, the embodiment of FIG. 9 does not include the first and second elongate linear edge portions 150, 152 as illustrated in FIG. 8. Instead, the medial portion 130 in the embodiment of FIG. 9 includes a first curved edge portion 156 and a second curved edge portion 158. The curved edge portions 156, 158 extend continuously along the entire length of the medial portion 130 in the same manner as the elongate linear edge portions 150, 152 described above. In addition, the term "elliptical" as used herein shall encompass the cross-sectional configuration of the medial portion 130 shown in the embodiments of both FIG. 8 and FIG. 9. Both of such embodiments will work with substantially equal effectiveness, and the selection of either embodiment will depend on a variety of factors, including but not limited to ease of manufacture, as well as flexibility of the materials used to produce the access site assembly 100. Furthermore, the thickness and width of the medial portion 130 in the embodiment of FIG. 9 will be substantially identical to the thickness and width of the medial portion 130 in the embodiment of FIG. 8.

Referring back to FIG. 8, the bore 138 is preferably elliptical in cross-section along the entire length thereof as previously noted. So that the bore 138 may readily and securely receive the body portion 12 (e.g. the medial section 18) of the needle apparatus 10 therein, the cross-sectional configuration of the bore 138 should closely approximate the cross-sectional configuration of the medial section 18 of the needle apparatus 10. Furthermore, the size of the bore 138 should be equal to or slightly larger than the size of the medial section 18 so that the medial section 18 may be readily inserted within the bore 138. However, the bore 138 should not be any larger than necessary relative to the medial section 18 in order to prevent fluid leakage between the needle apparatus 10 and the access site assembly 100 during use. The overall dimensions of the bore 138 may be selectively varied during manufacture of the access site assembly 100, depending on the size of needle apparatus 10 to be used therewith. However, in a preferred embodiment as shown in FIG. 8, the width "$W_3$" of the bore 138 will be about 0.10–0.30 inches, and the height "$H_1$" will be about 0.05–0.15 inches. As indicated above, the dimensions of the bore 138 should be equal to or greater than those of the medial section 18 of the needle apparatus 10 and, if necessary, should only exceed the dimensions of the medial section 18 by a minimal amount necessary to readily enable placement of the needle apparatus 10 within the bore 138. Accordingly, in a preferred embodiment, the width "$W_3$" of the bore 138 should not exceed the width "$W_1$" of the medial section 18 of the needle apparatus 10 by more than about 25%. Likewise, the height "$H_1$" of the bore 138 should not exceed the thickness "$T_1$" of the medial section 18 by more than 25% in a preferred embodiment. It should be noted that the dimensions of the medial section 18 and the bore 138 may, in fact, be approximately equal as indicated above since the preferred materials used to construct the tubular access port 120 enable it to slightly deform (e.g. stretch in a non-permanent manner) to accommodate a medial section 18 of substantially equal size.

Furthermore, in the embodiment of FIG. 8, the bore 138 will include non-curved, indented regions 160, 162 which are sized to respectively receive the elongate linear edge portions 60, 62 of the medial section 18 of the needle apparatus 10 shown in FIG. 3. This structural relationship will enable precise, mating engagement between the medial section 18 of the needle apparatus 10 illustrated in FIG. 3 and the tubular access port 120 of the access site assembly 100. As a result, fluid leakage between the needle apparatus 10 and the access port 120 is prevented.

In the alternative embodiment of FIG. 9, the structural and dimensional characteristics (e.g. thickness and width) of the bore 138 will be the same as those set forth in the primary embodiment of FIG. 8, with one exception. Specifically, the bore 138 will include curved, indented regions 164, 166 which are sized to respectively receive the first curved edge portion 72 and the second curved edge portion 74 of the medial section 18 in the alternative embodiment shown in FIG. 4. Again, this structural relationship will enable precise, mating engagement between the medial section 18 of the needle apparatus 10 illustrated in FIG. 4 and the tubular access port 120 of FIG. 9 so that fluid leakage between the needle apparatus 10 and the access port 120 is prevented.

It is preferred that the housing 101 of the access site assembly 100 described herein (e.g. the main conduit 102 and the tubular access port 120) be of single-piece construction and manufactured of an inert, flexible (e.g. compressible), and resilient plastic. Exemplary plastics suitable for this purpose would include but not be limited to flexible polyvinyl chloride, and thermoplastic elastomers known in the art. Furthermore, as indicated above with respect to the needle apparatus 10, it is preferred for health and safety reasons that the access site assembly 100 be disposed of when appropriate to avoid infection and the like.

Finally, with continued reference to FIGS. 6, 7, and 10-12, the access site assembly 100 further includes a resilient compression member 170 positioned on the medial portion 130 of the tubular access port 120. As shown in FIG. 10, the compression member 170 is preferably circular (e.g. annular) in cross-section, and includes an opening 172 therein. In a preferred embodiment, the opening 172 is elliptical in cross-section (FIG. 10), and is designed to substantially conform with the cross-sectional configuration of the medial portion 130 of the access port 120 shown in FIG. 8. However, the opening 172 will be sufficiently smaller in size than the medial portion 130 of the access port 120 so that, when mounted in position, the compression member 170 will compress the medial portion 130 (e.g. the side walls 140, 142) and thereby close the bore 138. To specifically accomplish this, the compression member 170 will be manufactured from a resilient, deformable, semi-rigid material (e.g. a flexible plastic such as polypropylene or polyethylene). The material used to manufacture the compression member should be of greater rigidity than the material used to produce the tubular access port 120. However, the term "deformable" as used herein shall again involve a structure which may be stretched to a limited degree and will return to its original configuration without permanent deformation. While the size of the opening 172 through the compression member 170 may be varied during production (e.g. depending on the dimensional characteristics of the tubular access port 120 to be used therewith) the opening 172 will preferably have a width "$W_4$" (FIG. 10) which is slightly greater than the width "$W_2$" of the tubular access port 120 when the access port 120 is in an open configuration as shown in FIG. 8. This dimensional relationship is designed to account for an elongation of the tubular access port 120 (e.g. an increase in the width "$W_2$" thereof) which occurs during compression of the port 120 by the compression member 170. In fact, the width "$W_4$" should be at least as large (and preferably no larger) than the width "$W_2$" of the tubular access port 120 when the access port 120 is in a closed configuration as shown in FIG. 7. In a specific and preferred embodiment, the width "$W_4$" of the opening 172 will be about 0.25–0.55 inches. Furthermore, it is preferred that the width "$W_4$" of the opening 172 be about 20% greater than the width "$W_2$" of the tubular access port 120 as measured prior to the compression thereof.

Conversely, the height "$H_2$" of the opening 172 (FIG. 10) will be considerably less than the thickness "$T_2$" of the tubular access port 120. As a result, placement of the compression member 170 on the access port 120 will cause compression of the side walls 140, 142 inwardly as desired (since the compression member 170 is made of a more rigid material than the access port 120). In a preferred embodiment, the height "$H_2$" of the opening 172 will be about 0.05–0.17 inches. Furthermore, the height "$H_2$" of the opening 172 will preferably be about 40–80% less than the thickness "$T_2$" of the medial portion 130 of the access port 120. Because the opening 172 is substantially narrower than the access port 120 (e.g. $H_2 < T_2$), the opening 172 shall, for the purposes of this invention, be considered smaller than the access port 120, thereby enabling compression of the port 120 by the compression member 170.

Furthermore, in the embodiment of FIG. 10, the opening 172 will include non-curved, indented regions 173, 174 which are sized to respectively receive the first and second elongate linear edge portions 150, 152 on the medial portion 130 of the access port 120 shown in the embodiment of FIGS. 6 and 8. This structural relationship will enable conforming engagement between the access port 120 in the embodiment of FIG. 8 and the opening 172 shown in FIG. 10 so that proper, effective, and complete compression of the port 120 may be accomplished.

FIG. 11 illustrates a cross-sectional view of a compression member 170 which has been modified in accordance with an alternative embodiment of the present invention. While the basic dimensions (e.g. width and thickness) of the opening 172 are substantially the same in the embodiments of FIGS. 10 and 11, the opening 172 in the embodiment of FIG. 11 does not include the non-curved, indented regions 173, 174 illustrated in FIG. 10. Instead, the opening 172 in the embodiment of FIG. 11 includes curved indented regions 176, 178 which are sized to respectively receive the curved edge portions 156, 158 of the medial portion 130 shown in the embodiment of FIG. 9. This structural relationship will again enable conforming engagement between the tubular access port 120 in the embodiment of FIG. 9 and the opening 172 shown in FIG. 11. As a result, proper, effective, and complete compression of the port 120 may be accomplished. In addition, the term "elliptical" as used herein shall encompass the cross-sectional configuration of the opening 172 shown in the embodiments of both FIG. 10 and FIG. 11.

In accordance with the foregoing general and specific dimensional characteristics described herein, the compression member 170 is readily mounted in position on the tubular access port 120 of the access site assembly 100. Prior to placement of the compression member 170 on the tubular access port 120, the bore 138 is in an open configuration as illustrated in FIGS. 6 and 8. To mount the compression member 170 in position, it is urged downwardly against the outer end 124 (and flange 132). Because the compression member 170 and the access port 120 are both flexible, the temporary deformation of such components will occur, thereby allowing placement of the compression member 170 onto the medial portion 130 of the access port 120. After placement of the compression member 170 on the medial portion 130, the compression member 170 will attempt to return to its original shape and configuration due to the resilient characteristics thereof. In view of this fact, and because the opening 172 is smaller than the medial portion 130 of the tubular access port 120, the compression member 170 will exert compressive forces on the medial portion 130. Because the access port 120 is manufactured of flexible, resilient material, the side walls 140, 142 thereof will flex inwardly, thereby closing (e.g. sealing) the bore 138 as shown in FIG. 7. With continued reference to FIG. 7, the mounted compression member 170 is positioned on the medial portion 130 of the tubular access port 120 between the inner end 122 and the outer end 124, and is maintained in position by the flange 132 which abuttingly engages the upper surface 189 of the compression member 170. The access site assembly 100 shown in FIG. 7 with the bore 138 in a closed orientation is now ready for use as described in detail below.

USE AND OPERATION

As indicated above, the present invention is especially useful in the withdrawal of bodily fluids (e.g. blood) from patients. Accordingly, the following description shall be made with reference to a fluid extraction procedure by medical personnel. However, notwithstanding the following description, the present invention (e.g. the above-described needle apparatus 10 and the access site assembly 100) may be used in an equally effective manner to introduce fluids (e.g. medicines and the like) into a patient. Thus, the present invention shall not be limited exclusively to the withdrawal of fluids (e.g. blood) as set forth below.

With reference to FIG. 12, the needle apparatus 10 of the present invention is attached to a conventional syringe 200 (shown in enlarged format partially in cross-section for the sake of clarity). The syringe 200 is of a type which is well known in the art (e.g. commercially available from Becton-Dickinson, Inc. of Rutherford, N.J. (USA), product number 9661. However, the needle apparatus 10 shall not be limited exclusively to the specific syringe 200 illustrated in FIG. 12, and may be used in connection with a wide variety of commercially available syringes. Furthermore, the needle apparatus 10 shall not be limited to exclusive use in connection with a syringe, and may also be attached to a wide variety of other medical fluid transfer devices (including conventional fluid extraction units which involve a sealed container having a vacuum therein). In such a system, the internal vacuum constitutes fluid transfer means for drawing fluids into the container. The needle apparatus 10 may therefore be used in connection with any fluid transfer device designed to receive or expel fluids therefrom, and the term "medical fluid transfer device" shall be deemed to encompass all devices with which the needle apparatus 10 may be used, including syringes. Furthermore, the term "medical fluid transfer device" shall also include but not be limited to conventional conduits or intravenous fluid lines wherein fluid materials (e.g. medicines and/or bodily fluids) may be received or withdrawn from a patient using the needle apparatus 10.

With continued reference to FIG. 12, syringe 200 includes a tubular reservoir chamber 202 having a continuous side wall 203, a first end 204, an open second end 206, and a slidable plunger 208 therein. The plunger 208 includes a resilient seal member 210 (e.g. made of soft synthetic rubber) conventionally secured thereto which is movably disposed within the interior region 212 of the reservoir chamber 202. The plunger 208 and associated seal member 210 constitute fluid transfer means in that they enable fluids to be drawn into or expelled from the reservoir chamber 202. The plunger 208 specifically consists of an elongate handle member 216 which extends partially outward from the open second end 206 of the reservoir chamber 202. The handle member 216 includes a first end 217 operatively connected to the seal member 210, and a second end 218 having a disk-like gripping member 220 integrally formed thereon. The first end 204 of the reservoir chamber 202 further includes an annular threaded portion 221 with a threaded region 222 on the interior surface 224 thereof.

The first end 204 of the reservoir chamber 202 likewise includes an end wall 226 having an opening 228 therein. Positioned directly over and in axial alignment with the opening 228 is a tubular member 232 having a passageway 234 therethrough as illustrated. In a preferred embodiment, the tubular member 232 is integrally formed as part of the end wall 226.

To secure the needle apparatus 10 to the first end 204 of the reservoir chamber 202, the distal end 16 is inserted within the threaded portion 221 so that the tabs 30 engage the threaded region 222. Thereafter, the entire needle apparatus 10 is rotated in a clockwise direction until the tubular member 232 firmly engages the inside walls 240 of the interior cavity 22 within the distal end 16 of the needle apparatus 10. The handle member 216 of the plunger 208 is then pushed downwardly until the seal member 210 is positioned substantially against the end wall 226 of the reservoir chamber 202. The syringe 200 with the needle apparatus 10 secured thereto is then ready for fluid transfer (e.g. withdrawal).

With continued reference to FIG. 12, the access site assembly 100 is illustrated in cross-section and in enlarged format for the sake of clarity. The first end 104 of the tubular main conduit 102 includes the proximal end 250 of a first fluid transfer tube 252 mounted therein, with the distal end 254 being in fluid communication with the circulatory system of a patient 256 (schematically illustrated in FIG. 12). The tube 252 is preferably manufactured of inert, flexible plastic (e.g. polyvinyl chloride), and has a diameter slightly larger than the diameter of the passageway 112 through the main conduit 102. As a result, secure frictional engagement of the proximal end 250 of the tube 252 within the passageway 112 at the first end 104 may occur. Alternatively, either the proximal end 250 of the tube 252, the interior walls 260 of the main conduit 102 or both of these components may be treated with a suitable solvent known in the art for medical use (e.g. cyclohexanol) which causes solvation (e.g. bonding) of the foregoing components together in a highly secure manner.

The second end 106 of the tubular main conduit 102 includes the proximal end 262 of a second fluid transfer tube 264 mounted therein, with the distal end 266 preferably being in fluid communication with a supply 268 of intravenously administered medicine (schematically illustrated in FIG. 12). The tube 264 is also preferably manufactured of inert, flexible plastic (e.g. polyvinyl chloride), and has a diameter slightly larger than the diameter of the passageway 112 through the main conduit 102. As a result, secure frictional engagement of the proximal end 262 of the tube 264 within the passageway 112 at the second end 106 will take place. Alternatively, as noted above, either the proximal end 262 of the tube 264, the interior walls 260 of the main conduit 102 or both of these components may be treated with a suitable solvent known in the art for medical use (e.g. cyclohexanol) which causes solvation (e.g. bonding) of the foregoing components together.

Prior to fluid withdrawal using the needle apparatus 10 of the present invention, the patient 256 in the embodiment of FIG. 12 is receiving medicine from the supply 268. The medicine initially travels from the supply 268 through the tube 264 which has a conventional in-line valve therein (not shown). Thereafter, the medicine flows into the passageway 112 of the main conduit 102, through the tube 252 and into the patient 256. Fluid leakage from the bore 138 in the tubular access port 120 is prevented by the compression member 170 which exerts compressive forces against the side walls 140, 142 of the access port 120. This causes the bore 138 to remain in a closed (e.g. sealed) configuration (FIG. 7) prior to introduction of the needle apparatus 10.

The needle apparatus 10 may then be used to withdraw fluid from the passageway 112 of the access site assembly 100 in a highly efficient manner. This fluid may consist of resident fluid (e.g. medicine), a mixture of blood and resident fluid, or undiluted blood, depending on the exact arrangement of additional components and other hardware (not shown) associated with the basic components schematically illustrated in FIG. 12. Accordingly, the present invention shall not be limited to any specific type of fluid to be withdrawn, but instead shall broadly encompass the withdrawal of any fluid which may be present within (e.g. passing through or residing in) the main conduit 102 of the access site assembly 100.

To withdraw fluid from the access site assembly 100, the body portion 12 of the needle apparatus 10 is centered over and placed in axial alignment with the closed bore 138 in the tubular access port 120. The proximal end 14 of the needle apparatus 10 is then urged into the bore 138, thereby forcing it open against the compressive forces exerted by the compression member 170 on the side walls 140, 142 of the access port 120. The needle apparatus 10 is continuously urged into the bore 138 until the proximal end 14 (including the terminal portion 76 and outlet 50) is positioned entirely within the passageway 112 of the main conduit 102. As a result, the proximal end 14 is positioned entirely within the fluid 300 (FIG. 12) to be withdrawn from the passageway 112. In this orientation, a substantial portion of the medial section 18 of the needle apparatus 10 is positioned within the bore 138. In the example of FIG. 12, the medial section 18 is positioned within the bore 138 up to the midpoint 280 of the medial section 18. During this procedure, fluid leakage between the needle apparatus 10 and the tubular access port 120 is effectively prevented by the compression member 170 which urges the side walls 140, 142 of the tubular access port 120 against the medial section 18 of the needle apparatus 10. In fact, the exertion of compressive forces by the compression member 170 creates a dynamic seal wherein fluid leakage is prevented even during movement of the needle apparatus 10 into the access site assembly 100. Fluid leakage is likewise prevented by the substantial conformity in cross-sectional configuration between the bore 138 and the medial section 18 as described above. Furthermore, the elliptical character of the tubular access port 120 and bore 138 makes the closure thereof around the medial section 18 of the needle apparatus 10 much easier and more complete compared with a non-elliptical (e.g. circular) access port which would be difficult to compress in a uniform manner.

To remove fluid, the valve (not shown) in the tube 264 is operated to prevent the further flow of medicine from the supply 268 into the access site assembly 100. Thereafter, any other appropriate components (not shown) which may be associated with the schematically-illustrated system of FIG. 12 are activated as necessary. Next, the gripping member 220 at the second end 218 of the handle member 216 associated with the plunger 208 is pulled in an outward direction. As a result, the seal member 210 is urged away from the end wall 226 in the reservoir chamber 202, thereby creating a vacuum in the chamber 202. This causes fluid to flow from the passageway 112 into the passageway 46 in the needle apparatus 10, and through the cavity 22 in the distal end 16 of the apparatus 10. Thereafter, the fluid passes into and through the passageway 234 of the tubular member 232, through the opening 228 in the end wall 226 of the reservoir chamber 202, and into the reservoir chamber 202. When the desired amount of fluid is collected, outward movement of the handle member 216 (and seal member 210) is discontinued. The needle apparatus 10 is then removed from the access site assembly 100 by pulling upwardly on the syringe 200. As a result, the medial section 18 and the proximal end 14 of the needle apparatus 10 are withdrawn from the bore 138 in the access port 120. During this procedure, the compression member 170 is continuously exerting compressive forces on the side walls 140, 142 of the access port 120, thereby urging the side walls 140, 142 against the medial section 18 of the needle apparatus 10. Accordingly, a dynamic seal is once again created between the access port 120 and the needle apparatus 10 which prevents fluid leakage therebetween. When the needle apparatus 10 is entirely removed from the bore 138 in the access port 120, the bore 138 is essentially self-sealing in that the compressive forces exerted by the compression member 170 again cause the bore 138 to revert to a closed orientation as shown in FIG. 7. In addition, after the syringe 200 and attached needle apparatus 10 are removed from the access site assembly 100, accidental tissue penetration into medical personnel by the needle apparatus 10 is effectively prevented by the blunt character of the terminal portion 76 of the apparatus 10 and the rounded end 78 associated therewith.

To deliver fluid materials (e.g. medicines and the like) using the syringe 200, needle apparatus 10, and access site assembly 100, the valve (not shown) in the tube 264 is again operated to prevent the further flow of medicine from the supply 268 into the access site assembly 100. Thereafter, any other appropriate components (not shown) which may be associated with the schematically-illustrated system of FIG. 12 are activated as necessary. Next, a syringe 200 having the needle apparatus 10 secured thereto is provided wherein the reservoir chamber 202 is filled with fluid to be delivered (e.g. liquid medicine). The body portion 12 of the needle apparatus 10 is centered over and placed in axial alignment with the closed bore 138 in the tubular access port 120. The proximal end 14 of the needle apparatus 10 is then urged into the bore 138, thereby forcing it open against the compressive forces exerted by the compression member 170 on the side walls 140, 142 of the access port 120. The needle apparatus 10 is continuously urged into the bore 138 until the proximal end 14 (including the terminal portion 76 and outlet 50) is positioned entirely within the passageway 112 of the main conduit 102. The gripping member 220 at the second end 218 of the handle member 216 associated with the plunger 208 is then pushed inwardly. This causes fluid materials to be expelled from the reservoir chamber 202 of the syringe 200 into the cavity 22 in the distal end 16 of the needle apparatus 10, and thereafter through the passageway 46 in the apparatus 10. The fluid then flows outwardly from the outlet 50 in the terminal portion 76 of the needle apparatus 10 and into the passageway 112 of the main conduit 102 in the access site assembly 100. Ultimately, the fluid thereafter flows through the tube 252 (FIG. 12) and into the patient 256. The needle apparatus 10 is then removed from the access site assembly 100 in the same manner described above when the syringe 200 was used to remove fluid materials from the access site assembly 100.

The present invention represents a considerable advance in the art of bodily fluid handling and withdrawal. Not only is accidental needle penetration of medical personnel eliminated, but the leakage of potentially infectious fluid is likewise prevented. All of these goals are accomplished using a medical system which is highly effective for its intended purposes, is easy to use, and is inexpensive to manufacture.

Having herein described preferred embodiments of the present invention, it is anticipated that suitable modifications may be made thereto by individuals skilled in the relevant art which nonetheless remain within the scope of the invention. For example, the present invention shall not be limited with respect to its applicability, construction materials, and dimensions which may be varied within the intended scope of the invention. Thus, the present invention shall only be construed in accordance with the following claims.

The invention that is claimed is:

1. A safety needle apparatus designed for attachment to a medical fluid transfer device, said needle apparatus comprising:
   a tubular body portion comprising a proximal end, a distal end, a medial section between said proximal end and said distal end, and a passageway extending continuously through said medial section from said proximal end to said distal end, said medial section being elliptical in cross-section from said proximal end of said body portion to said distal end thereof so as to create a flat external appearance, said distal end comprising a cavity therein, said cavity being in fluid communication with said passageway through said medial section of said body portion, said proximal end comprising a blunt terminal portion which prevents accidental penetration of said needle apparatus into a user thereof.

2. The needle apparatus of claim 1 wherein said body portion is comprised of an inert, resilient plastic.

3. The needle apparatus of claim 1 wherein said medial section comprises a first side wall and a second side wall, said first side wall comprising an arcuate exterior surface and said second side wall comprising an arcuate exterior surface, said first side wall being fixedly secured to said second side wall with said passageway therebetween, said arcuate exterior surface of said first side wall and said arcuate exterior surface of said second side wall having an equal radius of curvature.

4. A safety needle apparatus designed for attachment to a medical fluid transfer device, said needle apparatus comprising:
   a tubular body portion comprising a proximal end, a distal end, a medial section between said proximal end and said distal end, and a passageway extending continuously through said medial section from said proximal end to said distal end, said medial section being elliptical in cross-section from said proximal end of said body portion to said distal end thereof so as to create a flat external appearance;
   said distal end comprising a cavity therein, said cavity being in fluid communication with said passageway through said medial section of said body portion;
   said proximal end comprising a blunt terminal portion which prevents accidental penetration of said needle apparatus into a user thereof;
   said medial section comprising a first side wall and a second side wall, said first side wall comprising an arcuate exterior surface and said second side wall comprising an arcuate exterior surface, said first side wall being fixedly secured to said second side wall with said passageway therebetween, said arcuate exterior surface of said first side wall and said arcuate exterior surface of said second side wall having an equal radius of curvature; and
   said medial section further comprising a first elongate linear edge portion extending continuously along said medial section from said proximal end of said body portion to said distal end thereof, and a second elongate linear edge portion extending continuously along said medial section from said proximal end of said body portion to said distal end thereof, said first side wall and said second side wall being positioned between said first elongate linear edge portion and said second elongate linear edge portion.

5. An access site assembly for use in connection with a medical fluid transfer device comprising a safety needle apparatus secured thereto, said safety needle apparatus comprising a proximal end, a distal end, and a medial section therebetween, said access site assembly comprising:
  a tubular conduit comprising a first end, a second end, an intermediate section between said first end and said second end, and a passageway extending continuously through said intermediate section of said conduit from said first end to said second end thereof;
  an elongate tubular access port extending outwardly from said intermediate section of said conduit, said access port comprising a bore therethrough in fluid communication with said passageway, said bore being sized to receive at least a portion of said medial section of said needle apparatus therein, said access port being comprised of a flexible, resilient material, said access port and said bore both being elliptical in cross-section; and
  a deformable, resilient compression member comprising an opening therethrough, said compression member being positioned on said tubular access port so that said access port passes through said opening, said opening in said compression member having a size sufficiently small to enable said compression member to engage and compress said access port to thereby close said bore in said access port when said access site assembly is not in use.

6. The access site assembly of claim 5 wherein said tubular access port is comprised of an inert, resilient, and flexible plastic.

7. The access site assembly of claim 5 wherein said tubular access port is positioned at about a 90° angle relative to said intermediate section of said tubular conduit.

8. The access site assembly of claim 5 wherein said tubular access port further comprises a inner end, an outer end, and a medial portion between said inner end and said outer end, said inner end being affixed to said intermediate section of said tubular conduit, and said outer end comprising a flange extending outwardly therefrom, said compression member being positioned on said medial portion of said access port between said inner end and said flange at said outer end.

9. An access site assembly for use in connection with a medical fluid transfer device comprising a safety needle apparatus secured thereto, said safety needle apparatus comprising a proximal end, a distal end, and a medial section therebetween, said access site assembly comprising:
  a tubular conduit comprising a first end, a second end, an intermediate section between said first end and said second end, and a passageway extending continuously through said intermediate section of said conduit from said first end to said second end thereof;
  an elongate tubular access port extending outwardly from said intermediate section of said conduit, said access port comprising a bore therethrough in fluid communication with said passageway, said bore being sized to receive at least a portion of said medial section of said needle apparatus therein, said access port and said bore both being elliptical in cross-section, said access port being comprised of a flexible, resilient material; and
  a deformable, resilient compression member comprising an opening therethrough, said opening being elliptical in cross-section, said compression member being positioned on said tubular access port so that said access port passes through said opening, said opening in said compression member having a size sufficiently small to enable said compression member to engage and compress said access port to thereby close said bore in said access port when said access site assembly is not in use.

10. The access site assembly of claim 9 wherein said tubular access port is comprised of an inert, resilient, and flexible plastic.

11. The access site assembly of claim 9 wherein said tubular access port is positioned at about a 90° angle relative to said intermediate section of said tubular conduit.

12. The access site assembly of claim 9 wherein said tubular access port further comprises a inner end, an outer end, and a medial portion between said inner end and said outer end, said inner end being affixed to said intermediate section of said conduit, and said outer end comprising a flange extending outwardly therefrom, said compression member being positioned on said medial portion of said access port between said inner end and said flange at said outer end.

13. An access site assembly for use in connection with a medical fluid transfer device comprising a safety needle apparatus secured thereto, said safety needle apparatus comprising a proximal end, a distal end, and a medial section therebetween, said access site assembly comprising a housing, and an access port secured to said housing, said access port comprising a bore therethrough, said bore being sized to receive at least a portion of said medial section of said needle apparatus therein, said access port being comprised of a flexible, resilient material, said access site assembly further comprising a deformable, resilient compression member comprising an opening therethrough, said compression member being positioned on said access port so that said access port passes through said opening, said opening in said compression member having a size sufficiently small to enable said compression member to engage and compress said access port to thereby close said bore in said access port when said access site assembly is not in use.

14. A fluid transfer system comprising:
  a medical fluid transfer device comprising a needle apparatus secured thereto, said needle apparatus comprising:
    a tubular body portion comprising a proximal end, a distal end, a medial section between said proximal end and said distal end, and a passageway extending continuously through said medial section from said proximal end to said distal end, said medial section being elliptical in cross-section from said proximal end of said body portion to said distal end thereof so as to create a flat external appearance, said distal end comprising a cavity therein, said cavity being in fluid communication with said passageway through said medial section of said body portion, said proximal end comprising a blunt terminal portion which prevents accidental penetration of said needle apparatus into a user thereof; and an access site assembly sized to receive at least a portion of said medial section of said needle apparatus therein, said access site assembly comprising:
- a tubular conduit comprising a first end, a second end, an intermediate section between said first end and said second end, and a passageway extending continuously through said intermediate section of said conduit from said first end to said second end thereof;
- an elongate tubular access port extending outwardly from said intermediate section of said conduit, said access port comprising a bore therethrough in fluid communication with said passageway in said intermediate section of said conduit, said bore being sized to receive at least a portion of said medial section of said needle apparatus therein, said access port being comprised of a flexible, resilient material, said access port and said bore both being elliptical in cross-section; and
- a deformable, resilient compression member comprising an opening therethrough, said compression member being positioned on said tubular access port so that said access port passes through said opening, said opening in said compression member having a size sufficiently small to enable said compression member to engage and compress said access port to thereby close said bore in said access port when said access site assembly is not in use.

15. The fluid transfer system of claim 14 wherein said medial section of said needle apparatus comprises a first side wall and a second side wall, said first side wall comprising an arcuate exterior surface and said second side wall comprising an arcuate exterior surface, said first side wall being fixedly secured to said second side wall with said passageway in said medial section of said needle apparatus therebetween, said arcuate exterior surface of said first side wall and said arcuate exterior surface of said second side wall having an equal radius of curvature.

16. The fluid transfer system of claim 15 wherein said medial section of said needle apparatus further comprises a first elongate linear edge portion extending continuously along said medial section from said proximal end of said body portion to said distal end thereof, and a second elongate linear edge portion extending continuously along said medial section from said proximal end of said body portion to said distal end thereof, said first side wall and said second side wall being positioned between said first elongate linear edge portion and said second elongate linear edge portion.

17. The fluid transfer system of claim 14 wherein said opening through said compression member is elliptical in cross-section.

18. A fluid transfer system comprising:
a medical fluid transfer device comprising a needle apparatus secured thereto, said needle apparatus comprising:
- a tubular body portion comprising a proximal end, a distal end, a medial section between said proximal end and said distal end, and a passageway extending continuously through said medial section from said proximal end to said distal end, said medial section being elliptical in cross-section from said proximal end of said body portion to said distal end thereof so as to create a flat external appearance;
- said distal end comprising a cavity therein, said cavity being in fluid communication with said passageway through said medial section of said body portion;
- said proximal end comprising a blunt terminal portion which prevents accidental penetration of said needle apparatus into a user thereof;
- said medial section comprising a first side wall and a second side wall, said first side wall comprising an arcuate exterior surface and said second side wall comprising an arcuate exterior surface, said first side wall being fixedly secured to said second side wall with said passageway in said medial section of said needle apparatus therebetween, said arcuate exterior surface of said first side wall and said arcuate exterior surface of said second side wall having an equal radius of curvature; and
- said medial section further comprising a first elongate linear edge portion extending continuously along said medial section from said proximal end of said body portion to said distal end thereof, and a second elongate linear edge portion extending continuously along said medial section from said proximal end of said body portion to said distal end thereof, said first side wall and said second side wall being positioned between said first elongate linear edge portion and said second elongate linear edge portion; and an access site assembly sized to receive at least a portion of said medial section of said needle apparatus therein, said access site assembly comprising:
- a tubular conduit comprising a first end, a second end, an intermediate section between said first end and said second end, and a passageway extending continuously through said intermediate section of said conduit from said first end to said second end thereof;
- an elongate tubular access port extending outwardly from said intermediate section of said conduit, said access port comprising a bore therethrough in fluid communication with said passageway in said intermediate section of said conduit, said bore being sized to receive at least a portion of said medial section of said needle apparatus therein, said access port and said bore both being elliptical in cross-section, said access port being comprised of a flexible, resilient material; and
- a deformable, resilient compression member comprising an opening therethrough, said opening being elliptical in cross-section, said compression member being positioned on said access port so that said access port passes through said opening, said opening in said compression member having a size sufficiently small to enable said compression member to engage and compress said access port to thereby close said bore in said access port when said access site assembly is not in use.

* * * * *